US00PP14417P29

(12) United States Plant Patent
Magee

(10) Patent No.: US PP14,417 P2
(45) Date of Patent: Dec. 23, 2003

(54) ILEX HYBRID PLANT NAMED 'MAGLAND'

(50) Latin Name: *(Ilex cornuta×Ilex pernyi)×Ilex latifolia*
Varietal Denomination: Magland

(75) Inventor: Jack Mitchell Magee, Poplarville, MS (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 10/201,827

(22) Filed: Jul. 25, 2002

(51) Int. Cl.[7] ..... A01H 5/00
(52) U.S. Cl. ..... Plt./247
(58) Field of Search ..... Plt./247

*Primary Examiner*—Kent Bell

(57) ABSTRACT

A new and distinct variety of Ilex plant found as a branch sport of Ilex hybrid 'Conaf' U.S. Plant Pat. No. 9,487. The new variety possesses a dense, upright, pyramidal growth habit, flowers which produce functional pollen and ovaries, attractive orange-red fruit, unusual dull green foliage, and distinctly arranged leaf serrations.

1 Drawing Sheet

Genus species: (*Ilex cornuta×Ilex pernyi*)×*Ilex latifolia*.
Varietal denomination: 'Magland'.

BACKGROUND OF THE INVENTION

The present invention relates to a new distinct variety of Ilex hereinafter referred to by the name 'Magland'. This new Ilex variety was discovered by Jack Mitchell Magee in April, 1994 as a naturally occurring branch sport of Ilex hybrid 'Conaf' U.S. Plant Pat No. 9,487 while being grown at Evergreen Nursery in Poplarville, Miss. The value of this new cultivar lies in its dense, upright, pyramidal growth habit, attractive orange-red fruit, and unusual leaf serrations. As with the parent plant, the plant of this invention may be advantageously employed as a specimen appointment, in either formal or informal groupings, and is very attractive in mass plantings. The plant serves well in foundation plantings and is adapted for culture as a potted plant. This plant is responsive to pruning and training and may be used in forming attractive hedges and maintained without an excessive amount of care.

Asexual propagation of the new plant by cuttings has been under Mr. Magee's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Poplarville, Miss.

1. Dense, upright, and pyramidal in nature.
2. Hardy to Zone 7.
3. Heat and drought tolerant.
4. Fast growth rate under normal fertilization and moisture conditions.
5. Tolerates most soils from moist to dry and from sand to clay.
6. Relatively pest resistant.
7. Very desirable in planters.
8. Make a good hedge or screen.

9. Easy to root from cuttings collected any time of year.
10. Flowers are perfect and can effectively pollinate other form of Ilex.
11. Produces attractive orange-red fruit in the fall which persist into the winter and which may result in bird visitations.
12. Has the ability to be sheared and trimmed to be kept within prescribed limits.
13. Mature leaves are a dull green color with attractive spines.
14. Easily trained into a small tree.

DESCRIPTION OF THE DRAWINGS

This new Ilex hybrid variety is illustrated by the accompanying photographic prints in which:

1. The photograph at the top of the sheet is a close-up view of the attractive orange-red fruit and mature foliage of the new variety.
2. The photograph at the bottom of the sheet is a side-by-side photograph of (from left to right) Ilex hybrid 'Magland', Ilex hybrid 'Conaf' U.S. Plant Pat. No. 9,487, and Ilex hybrid 'Mary Nell'. The photograph, which was taken in mid-winter, shows the new varietys dense, upright, and pyramidal growth habit.

The colors shown are as true as is reasonably possible to obtain by conventional photographic procedures. Colors in the photographs may appear different than actual colors due to light reflectance. The colors of the various plant parts are defined with references to The Royal Horticultural Society Colour Chart. Descriptions of colors in ordinary terms are presented where appropriate for clarity in meaning.

BOTANICAL DESCRIPTION OF THE PLANT

The following is a detailed description of the new variety of Ilex based on my observations made a 2 year old plants grown in 3 gallon containers in wholesale commercial production practices, in greenhouses, and in established landscape plantings in Poplarville, Miss.

DISTINCTIVE CHARACTERISTICS

TABLE 1

| Characteristic | Ilex hybrid 'Magland' | Ilex hybrid 'Conaf' PP#9,487 | Ilex hybrid 'Mary Nell' |
|---|---|---|---|
| Height (Mature) | 12–15' | 15–20' | 15–25' |
| Width (Mature) | 8–10' | 12–15' | 12–15' |
| Leaf Length | 2–2¾" | 2–3½" | 2⅝–3½" |
| Leaf Width | 1–1⅜" | 1⅛–1⅝" | 1⅛–1¾" |
| Internode Length | ¼–½" | ½–¾" | ⅝–1¼" |
| Leaf Glossiness (Mature) | Dull | Dull | Very Glossy |
| Leaf Shape | Ovate lanceolate | Ovate lanceolate | Ovate to broadly lanceolate |
| Leaf Spines (Pairs) | 3–5 | 3–5 | 9–11 |
| Terminal Spines | 3 | 3 | 1 |
| Fruit Color | Orange-Red G. 33A | Orange-Red G. 33A | Red G. 40A |
| Flowers Sex | Male & Female | Male & Female | Female Only |
| Mature Shape | Dense, upright, pyramidal | Upright, pyramidal | Upright, pyramidal |

'Magland' originated as a naturally occurring branch sport of Ilex hybrid 'Conaf' U.S. Plant Pat. No. 9,487 which I found in 1989 as an openly pollinated seedling of the non-patented plant Ilex hybrid 'Mary Nell'. 'Magland' is similar to Ilex hybrid 'Conaf', however in side-by-side comparisons in Poplarville, Miss. they differ in growth habit, foliage size, and internode length.

Ilex hybrid 'Mary Nell' originated from a controlled cross made in 1962 by Joe McDaniel in Semmes, Ala. The female parent was *Ilex cornuta*×*Ilex pernyi* 'Red Delight' (unpatented), named and introduced by Henry Hohman in Kingxville, Md. The male parent was *Ilex latifolia.* Ilex hybrid 'Mary Nell' was named in 1981 by Thomas H. Dodd, Jr. after Joe McDaniel's wife. This plant is comparable to the new plant; however, there are many differences, the most obvious being the foliage shape and number of spines.

Classification:
Botanical: (*Ilex cornuta*×*Ilex pernyi*)×*Ilex latifolia.*
Form: Dense,upright, and pyramidal.
Height: 12–15'.
Width: 8–10'.
Growth habit: Shrub or small tree.
Growth rate: Fast under normal fertilization and moisture conditions. Reaches mature height of 12 to 15 feet and width of 8 to 10 feet in 8 to 10 years.
Foliage: Alternate, simple, evergreen, ovate to lanceolate, and varying in size from 2" to 2¾" long and 1" to 1⅜" wide. The margins are serrate with 3 to 5 pairs of prominent spines.

The spines vary in length and width from ⅛" to ¼" on the plant but spines on each leaf are almost uniform in size. The apex is acute with 3 terminal spines and the base is obtuse. The petiole is 3/16" to 5/16" long with a 1/16" to 3/32" diameter. Mid-veins and laterals are impressed on the upper leaf surface and the mid-veins are prominent on the underside. Immature mid and lateral veins are Yellow-Green Group 144B top and bottom and mature to Yellow-Green Group 146D. The upper surface of the immature leaf is semi-glossy, glabrous, and is Yellow-Green Group 144A. The lower surface of the immature leaf is Yellow-Green Group 144A and matte. As the leaves mature they become less glossy and the upper surface becomes closest to Green Group 139A and the lower leaf surface becomes Yellow-Green Group 146C. This mature leaf color persists throughout the winter. Although the mature leaf color of the new variety is closest to Green Group 139A, it appears to be a shade lighter when viewed in full sun. This could be due to the dull leaf surface of the new variety.

In 1997, the date of initial spring growth was March 21, in Poplarville, Miss. After the initial spring flush, there was almost continuous growth until fall, ending October 25, also in Poplarville, Miss. This growth pattern was identical to the parent plant. When grown in full sun, the internode length of this plant is ¼" to ½" compared to ½" to ¾" for the parent plant. When grown in light shade, the internode length is ⅝" to ⅞". As would be expected, either plant grown in the shade results in a taller, less dense plant with larger leaves.

The average length of terminal growth of the initial spring flush is about 10" for a plant in full sun and about 12" when grown in shade. After this initial flush we normally trim the plant lightly and the plant then continues to grow about 6" until we trim it a second time in the early fall. The fall growth of about 8" then hides the cut limbs. We finish in the fall with a three gallon plant about 28" tall and 24" wide. I have not noticed a difference in vigor between this plant and the parent. In the landscape, little or no pruning is necessary to produce a dense and pyramidal shrub in full sun. In shade, however, some trimming may be needed to produce the same effect. The lower limbs can be removed to produce a small tree with attractive gray-brown bark.

Stems: The young shoots and petioles are Yellow-Green Group 144A, glabrous, and matte. After one or more years the stems are generally Grey-Brown Group 199C, glabrous and rugose. The pith is solid and uniform.
Flowers: Perfect, small, creamy yellow, inconspicuous, slightly fragrant, borne on previous season's growth from March to May. Buds are globular, 1/16" to 1/18" in diameter, Yellow-Green Group 144A, and without foliaceous appendages. Flowers are clustered in the leaf axils and are 4-merous. Unbranched pedicels are about ¼" long and Yellow-Green Group 144A. The four ovate sepals are persistent, glabrous, 1/32" to 1/16" wide, 1–16" to 3/32" long. Yellow-Green Group 144A (upper and lower surfaces), and united at the base. The sepals have acute apices and entire margins. The four ovate petals are 1/16" to ⅛" wide, ⅛" to 3/16" long, Yellow-Group 2D (upper and lower surfaces), arranged regularly, united at the base, and imbricate in bud. The petals have obtuse apices and entire margins. The ovary protrudes from the receptacle and is Green Group 143A. The ovary is devoid of styles and the stigma is discoid and lobed. There are four 1/18" long stamens with immature anthers which are White Group 155D. As the anthers mature and pollen is released the color becomes Yellow Group 3C. Pollen production is moderate. Blooms are small to medium in size, Yellow Group 2D, ⅜" in diameter, and last on the plant in the garden two to four days.
Fruit: Drupaceous, globose, ¼" to ⅜" diameter, borne fasciculate with two to five fruits on short unbranched pedicels ¼" long. Each fruit contains four pyrenes. Matures to Orange-Red Group 33A in mid-November in Poplarville, Miss. and persists into the winter. Normally, fruit set is heavy.
Culture: Grows well in a wide range of conditions and tolerates sun to part shade. Grows in nearly any soil type, from moist to very dry and sand to clay. Responds well to mulching and medium applications of fertilizer; prefers PH 5 to 6.5. Little pruning is needed. Can be sheared. Disease and pest resistance is comparable to Ilex hybrid 'Conaf'. Propagated with semi-hardwood cuttings any time of year. Cuttings taken in late spring initiate roots in 6 to 8 weeks and are well rooted in 4 to 5 months. The root system is fibrous and rapidly established.

I claim:

1. A new and distinct variety of Ilex plant named 'Magland', as illustrated and described.

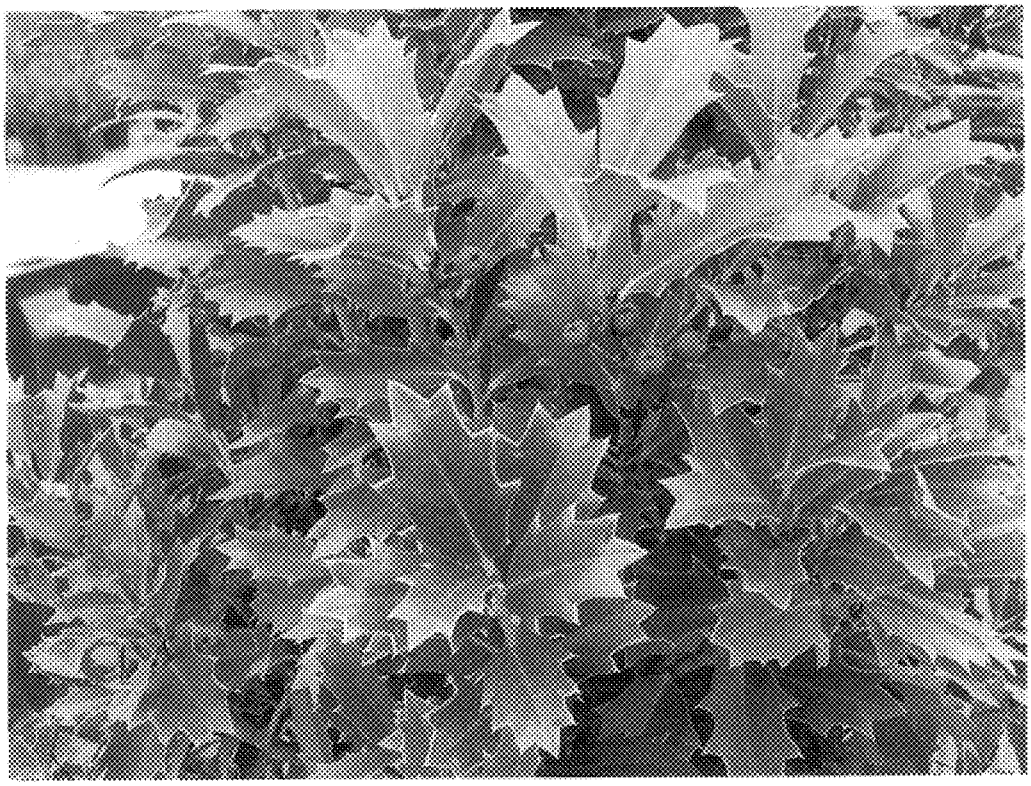
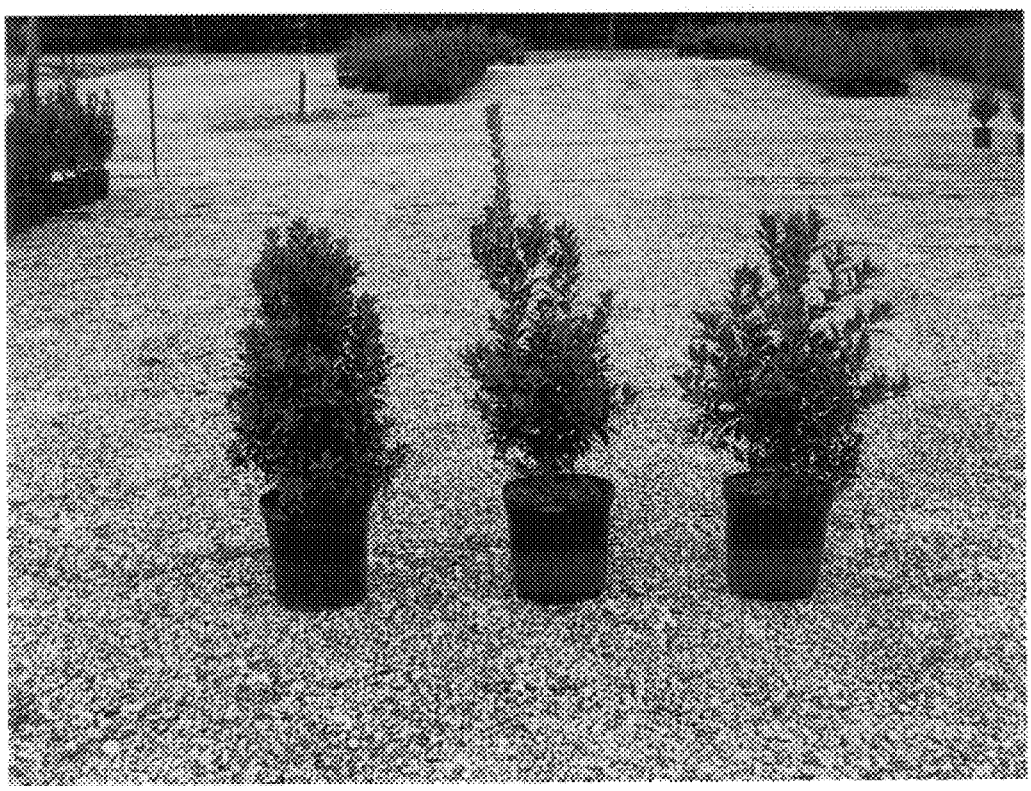

* * * * *